United States Patent
Rayasam

(10) Patent No.: US 12,283,368 B2
(45) Date of Patent: Apr. 22, 2025

(54) METHOD AND DEVICE FOR DETERMINING PRESENCE OF A TUMOR

(71) Applicant: Siemens Healthcare GmbH, Erlangen (DE)

(72) Inventor: Suparna Rayasam, Karnataka (IN)

(73) Assignee: Siemens Healthineers AG, Forchheim (DE)

( * ) Notice: Subject to any disclaimer, the term of this patent is extended or adjusted under 35 U.S.C. 154(b) by 378 days.

(21) Appl. No.: 17/829,318

(22) Filed: May 31, 2022

(65) Prior Publication Data
US 2022/0392618 A1    Dec. 8, 2022

(30) Foreign Application Priority Data

Jun. 2, 2021 (EP) ..................... 21177295

(51) Int. Cl.
*G16H 30/40* (2018.01)
*A61B 5/00* (2006.01)
(Continued)

(52) U.S. Cl.
CPC .............. *G16H 30/40* (2018.01); *A61B 5/004* (2013.01); *G06N 20/00* (2019.01); *G06T 7/0012* (2013.01); *G06T 7/174* (2017.01); *G06V 10/751* (2022.01); *G06T 2207/30096* (2013.01); *G06T 2207/30101* (2013.01)

(58) Field of Classification Search
CPC ....... G16H 30/40; G06T 7/174; G06T 7/0012; G06N 20/00; G06V 10/751; A61B 5/004
See application file for complete search history.

(56) References Cited

U.S. PATENT DOCUMENTS

2007/0019846 A1    1/2007  Bullitt et al.
2010/0027863 A1    2/2010  Venkataraman et al.
(Continued)

FOREIGN PATENT DOCUMENTS

JP    2019154571 A    9/2019

OTHER PUBLICATIONS

Iwazawa, Jan et al, Clinical utility and limitations of tumor-feeder detection software for liver cancer embolization, European Journal of Radiology; Elsevier; vol. 82; 2013; 7pp.
(Continued)

*Primary Examiner* — David Bilodeau
(74) *Attorney, Agent, or Firm* — Lempia Summerfield Katz LLC

(57) ABSTRACT

A method and a device for determining a presence of tumor are provided. The method includes receiving a medical image associated with a patient. The medical image includes a region of interest associated with the patient. The method includes identifying one or more blood vessels associated with the region of interest in the medical image. The method includes determining a set of characteristics associated with the one or more blood vessels using a trained machine learning model. The method also includes determining whether the one or more blood vessels are feeder vessels associated with the tumor based on the set of characteristics associated with the one or more blood vessels. The method includes detecting a tumor region in the region of interest based on the feeder vessels, when the one or more blood vessels are the feeder vessels associated with the tumor.

17 Claims, 6 Drawing Sheets

(51) Int. Cl.
*G06N 20/00* (2019.01)
*G06T 7/00* (2017.01)
*G06T 7/174* (2017.01)
*G06V 10/75* (2022.01)

(56) References Cited

U.S. PATENT DOCUMENTS

| | | |
|---|---|---|
| 2012/0014573 A1 | 1/2012 | Lautenschlaeger et al. |
| 2014/0296842 A1* | 10/2014 | Mansi .................... A61B 34/10 703/2 |
| 2015/0056190 A1* | 2/2015 | Hegde .............. G01N 33/57415 436/86 |
| 2015/0265162 A1* | 9/2015 | Lavi .................... A61B 6/5217 600/408 |
| 2015/0324962 A1* | 11/2015 | Itu .......................... G16H 30/40 382/130 |
| 2017/0296275 A1 | 10/2017 | Chapiro et al. |
| 2018/0005085 A1 | 1/2018 | Kakileti |
| 2019/0125193 A1* | 5/2019 | Saito .................... A61B 6/481 |

OTHER PUBLICATIONS

Jain, Rakesh K, Molecular regulation of vessel maturation, Nature Medicine, vol. 9, No. 6, pp. 685-693, Jun. 2003.

* cited by examiner

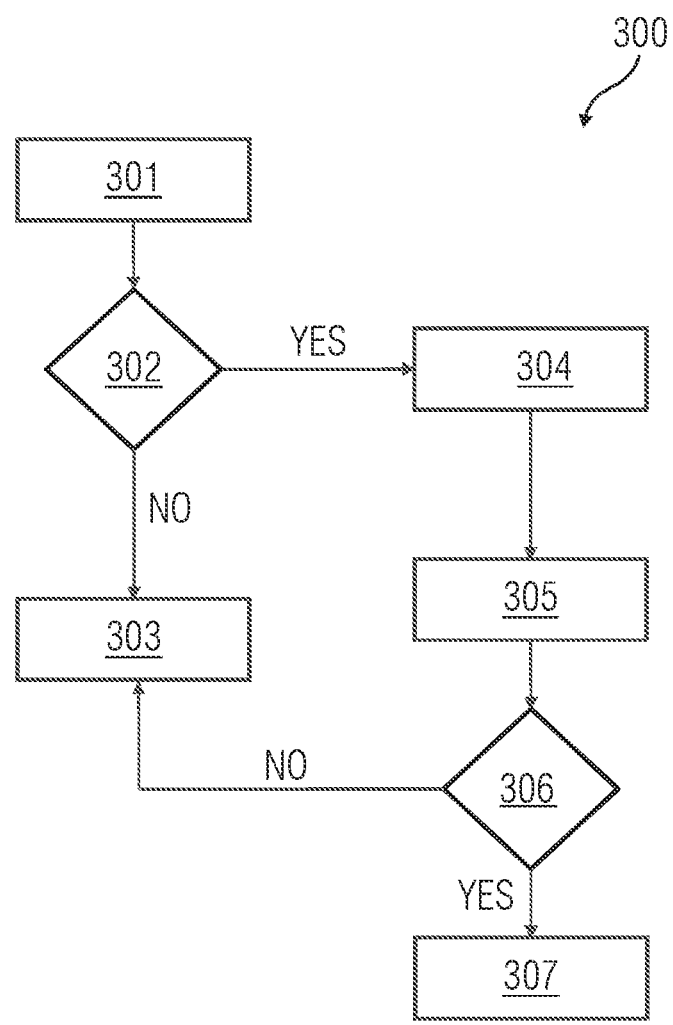

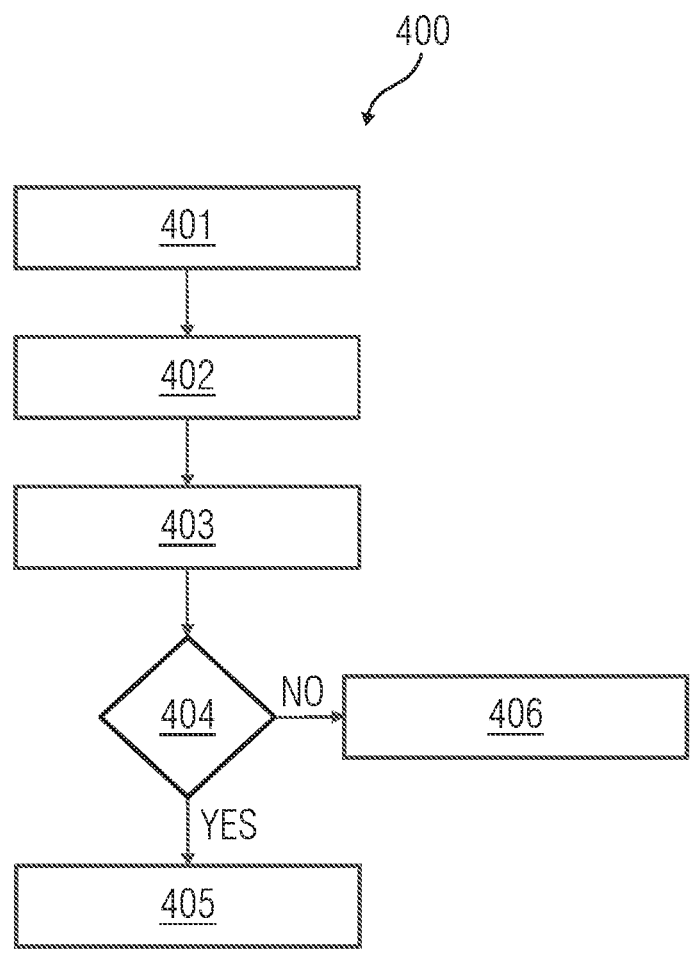

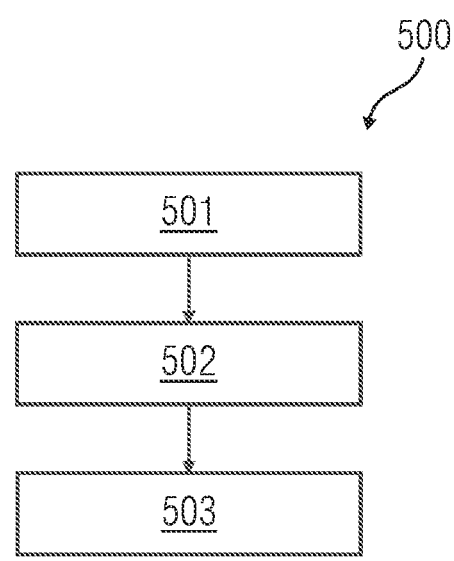

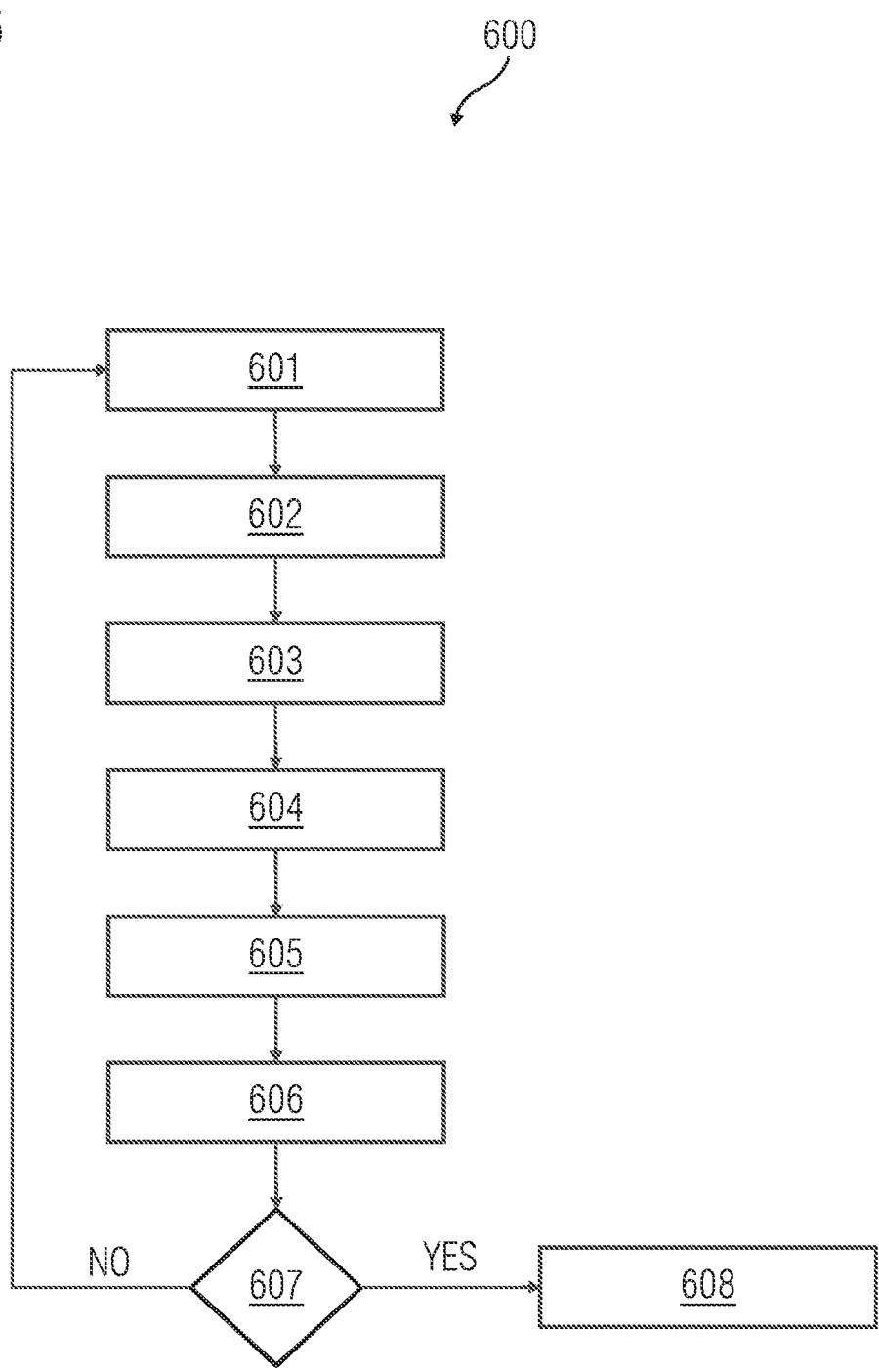

METHOD AND DEVICE FOR DETERMINING PRESENCE OF A TUMOR

PRIORITY

This application claims the benefit of European Patent Application No. EP 21177295.9, filed on Jun. 2, 2021, which is hereby incorporated by reference in its entirety.

FIELD OF TECHNOLOGY

The present embodiments relate to a method and a device for determining a presence of a tumor in a patient.

BACKGROUND

Cancer is one of the major causes of fatality in the world. Therefore, the need of the hour is to effectively treat tumors. One of the methods to treat tumors includes embolization, which is a procedure involving injection of substances directly into an artery to block or reduce blood flow to the tumor in a region. Current methods of detecting blood vessels are dependent on an experience of a physician to mark blood vessels that appear to feed the tumor (also known as feeder vessels). Therefore, the physical and biological characteristics of such blood vessels may not be considered during embolization procedure. This may lead to identification of normal tissues as tumor tissues, thereby damaging healthy tissues in the patient and missing some areas of the tumor.

SUMMARY AND DESCRIPTION

The scope of the present invention is defined solely by the appended claims and is not affected to any degree by the statements within this summary.

Currently, there is no way to identify feeder vessels and an associated tumor region for cancer treatments, that is effective and accurate.

The present embodiments may obviate one or more of the drawbacks or limitations in the related art. For example, a method and a device that enable effective determination of presence of a tumor in a patient are provided.

In one embodiment, a method of determining a presence of a tumor in a patient is provided. The method includes receiving a medical image associated with the patient. The medical image includes a region of interest associated with the patient. In an embodiment, the medical image may be a computed tomography angiography image, an X-ray angiography image, or a magnetic resonance imaging image. The medical image may be received from a medical imaging device such as an X-ray imaging device, computed tomography imaging device, MRI device, etc. The region of interest imaged in the medical image may be a region in the body of the patient suspected to include a tumor. In a further embodiment, the region of interest in the medical image may include one or more organs associated with the patient, vasculature associated with the patient, and/or bone or tissue information associated with the patient.

The method further includes identifying one or more blood vessels associated with the region of interest. For example, the blood vessels to be identified may include the blood vessels that may supply blood to the tumor present in the region of interest. In an embodiment, the blood vessels in the medical image may be segmented using one or more segmentation techniques that may be known to a person skilled in the art. For example, a region growing algorithm may be used to segment the blood vessels. The region growing algorithm segments the blood vessels based on pixel information associated with the blood vessels in the medical image. In a further embodiment, the segmented blood vessels may be skeletonized using topology preserving thinning algorithm. In one embodiment, skeletonizing the blood vessels preserves the topology of the blood vessels.

The method further includes determining a set of characteristics associated with the blood vessels. This may be performed using a trained machine learning model. The set of characteristics may include, for example, a diameter associated with the blood vessels, branching of the blood vessels, and/or tortuosity of the blood vessels. Since the blood vessels that supply blood to a tumor are created by the tumor itself, the morphological characteristics associated with such blood vessels are different over normal blood vessels. For example, in case of tumor vasculature, the diameter associated with the blood vessels is irregular or uneven. Similarly, the branching of such blood vessels is abnormal, and the blood vessel network is chaotic (e.g., there may be no hierarchy in blood vessels such as arteries, arterioles, capillaries, venules, and veins). Therefore, the machine learning model may be trained to detect such abnormal characteristics in the blood vessels segmented from the medical image. Further, the method includes determining whether the blood vessels are feeder vessels associated with the tumor based on the set of characteristics associated with the blood vessels. Feeder vessels are the blood vessels that supply blood to the tumor. The method further includes detecting a tumor region in the region of interest based on the feeder vessels. In an embodiment, the tumor region may be identified based on the network of the feeder vessels in the region of interest. In one embodiment, the method enables accurate identification of tumor vasculature, thereby making the embolization process accurate and more effective. Yet another advantage of the present embodiments is that damage to the healthy tissue associated with the patient is reduced.

According to an embodiment, determining if the blood vessels are feeder vessels associated with the tumor includes measuring a diameter associated with the blood vessels using the trained machine learning model. In an embodiment, the diameter may be a Euclidian distance between two points, where a first point of the two points lies on a parallel wall of the blood vessel from a second point of the two points. The method further includes determining if the diameter of the blood vessels decrease as the blood vessels branch into branching vessels. In a normal vasculature, the diameter of a parent blood vessel is always more than a diameter of the branching vessel. Therefore, as the blood vessel progresses along, starting from the parent blood vessel, the diameter of the blood vessel should decrease. However, this may not be true for feeder vessels. The method further includes classifying the blood vessels to be feeder vessels associated with the tumor if the diameter of the blood vessels does not decrease as the blood vessels branch into branching vessels. In one embodiment, the machine learning model enables effective identification of feeder vessel based on the diameter of the blood vessels. Yet another advantage of the present embodiments is that blood vessels associated with healthy tissue of the patient are not damaged due to cancer therapy.

According to another embodiment, determining if the blood vessels are feeder vessels associated with the tumor includes determining a radius associated with the blood vessels. Further, a radius associated with the branching vessels originating from the blood vessels is also determined. The branching vessels mostly obey Murray's law, according to which a cube of the radius of the blood vessel equals a sum of cubes of the radii of the branching vessels. Therefore, the method further includes computing a cube of the radius associated with the blood vessels and the radius associated with the branching vessels. Further, it is determined if the cube of the radius of the blood vessel equals a sum of cubes of the radii of the branching vessels. If the radius of the blood vessel does not equal a sum of cubes of the radii of the branching vessels, the blood vessel is classified as the feeder vessel associated with the tumor using the trained machine learning model. In one embodiment, the machine learning model enables determining if there exists an irregular branching associated with the blood vessels. This may be a characteristic of feeder vessels associated with the tumor. Therefore, embolization may be accurately performed.

According to yet another embodiment, determining if the blood vessels are feeder vessels associated with the tumor includes determining the tortuosity of the blood vessels. Tortuosity of the blood vessels is determined based on an angular deviation of the blood vessels from a straight path associated with the blood vessels. This may be performed using the trained machine learning model. Tortuosity enables understanding if the blood vessels are chaotic in nature. In an embodiment, the tortuosity of the blood vessels may be determined using a distance metric method or a sum of angles metric method. The method further includes comparing the tortuosity of the blood vessels with a pre-determined standard associated with the blood vessels using a trained machine learning model. For example, if the blood vessels have two or more consecutive curvatures having angles greater than or equal to 180°, the blood vessel may be considered to be severely tortuous. Further, the method includes classifying the blood vessels as feeder vessels if the tortuosity of the blood vessels does not match the predetermined standard. In an embodiment, the measure of tortuosity of the blood vessels may be considered along with a diameter of the blood vessels and/or a chaotic feature of the blood vessel network to determine if the blood vessel is a feeder vessel. In one embodiment, the present embodiments enable accurate identification of feeder vessels for cancer therapy. Additionally, the tumor region may also be accurately identified based on the feeder vessel network.

According to an embodiment, determining the tumor region in the region of interest based on the feeder vessels includes identifying a region in the medical image based on the classified feeder vessels, where the identified region in the medical image is an area surrounding the feeder vessels. For example, the feeder vessels may be traced to identify the region where the feeder vessels drain. For example, the feeder vessels may drain in a region where the feeder vessels end. Such region may be marked and labelled as a region surrounding the feeder vessels. Further, the method includes determining a pixel intensity associated with the region of interest in the medical image. The pixel intensity may be the pixel values associated with the pixels in the medical image. The method includes determining the tumor region based on the pixel intensity and the region surrounding the feeder vessels. The tumor region has a pixel intensity greater than the pixel intensity of the other regions in the medical image. For example, connected component analysis may be performed to accurately identify the tumor region in the medical image. Connected component analysis enables identification of the tumor region based on pixel intensities associated with the medical image. In one embodiment, the present embodiments enable accurate determination of the tumor region and the associated feeder vessels, based on which the cancer therapy may be effectively planned for the patient.

According to another embodiment, the trained machine learning model is a classification and regression tree (CART) model. The model is a supervised machine learning model that may classify medical images as normal or suspected to include a tumor with feeder vessels. The CART model may perform the classification based on diameter associated with the blood vessels, branching of the blood vessels, and/or tortuosity of the blood vessels in the medical image. In an embodiment, the model may use Gini index to create decision points for performing classification. The Gini index stores a sum of squared probabilities of each class. The Gini index may be represented as:

$$\text{Gini} = 1 - \sum_{i=1}^{n} (Pi)^2$$

i is a number of classes, and Pi is a probability of each class.

In one embodiment, the model is configured to accurately identify a tumor region in the medical image along with the feeder vessels, thereby enabling effective cancer therapy to the patient.

In another embodiment, a method of training a machine learning model for determining a presence of tumor in a patient is provided. The method includes receiving a medical image associated with a patient, where the medical image includes a region of interest associated with the patient. The medical image may be received from a source such as medical database or a medical imaging device. Additionally, the method includes identifying one or more blood vessels associated with the region of interest. Additionally, the method includes receiving the machine learning model and determining, by the model, a set of characteristics associated with the blood vessels. The method further includes determining, by the machine learning model, if the blood vessels are feeder vessels associated with the tumor based on the set of characteristics associated with the blood vessels.

The method further includes receiving tumor data related to the medical dataset, where the tumor data indicates if the blood vessels are feeder vessels associated with the tumor. In an embodiment, the tumor data may include a medical image that has been labelled to indicate the presence or absence of feeder vessels associated with a tumor in a patient. In a further embodiment, the labelled tumor data may be associated with a plurality of patients historically monitored and treated for cancer. In an alternate embodiment, the tumor data may be data received from a physician/expert that may include an analysis of the medical image associated with the patient, indicating the presence or absence of feeder vessels associated with the patient.

The method further includes adjusting the machine learning model based on an outcome of comparison between the feeder vessels determined by the model and the tumor data. The comparison may indicate an accuracy of the detection of feeder vessels by the machine learning model. Therefore, the machine learning model may be adjusted if a difference between the determined feeder vessels and the tumor data is identified in the comparison. In one embodiment, the machine learning model is made more robust, thereby improving the accuracy with which the feeder vessels are determined by the model. Therefore, determination of presence of tumor in the patient may be made effective and accurate.

In yet another embodiment, a device for determining a presence of tumor in a patient is provided. The device includes one or more processing units, a medical database coupled to the one or more processing units, the medical database including a plurality of medical images associated with the patient, and tumor data. The device further includes a memory coupled to the one or more processing units. The memory includes a tumor determination module configured to perform the method acts as described above, using at least one trained machine learning model.

The present embodiments relate, in one aspect, to a non-transitory computer-readable storage medium storing machine-readable instructions therein, that when executed by a processor, cause the processor to receive a medical image associated with the patient. The medical image includes a region of interest associated with the patient. The machine-readable instructions further include identify one or more blood vessels associated with the region of interest in the medical image, determining a set of characteristics associated with the blood vessels using a trained machine learning model and determining, using the trained machine learning model, if the blood vessels are feeder vessels associated with the tumor based on the set of characteristics associated with the blood vessels. The machine-readable instructions further include detecting a tumor region in the region of interest based on the feeder vessels, when the blood vessels are feeder vessels associated with the tumor.

BRIEF DESCRIPTION OF THE DRAWINGS

The present invention is further described hereinafter with reference to illustrated embodiments shown in the accompanying drawings, in which:

FIG. 3 illustrates a flowchart of a method of determining if the blood vessels are feeder vessels associated with the tumor, according to an embodiment.

FIG. 4 illustrates a flowchart of a method of determining if the blood vessels are feeder vessels associated with the tumor, according to another embodiment.

FIG. 5 illustrates a flowchart of a method of detecting the tumor region in the region of interest based on the feeder vessels, according to an embodiment.

FIG. 6 illustrates a flowchart of a method of training a machine learning model to determine a presence of a tumor in a patient, according to an embodiment.

DETAILED DESCRIPTION

Figure 1:
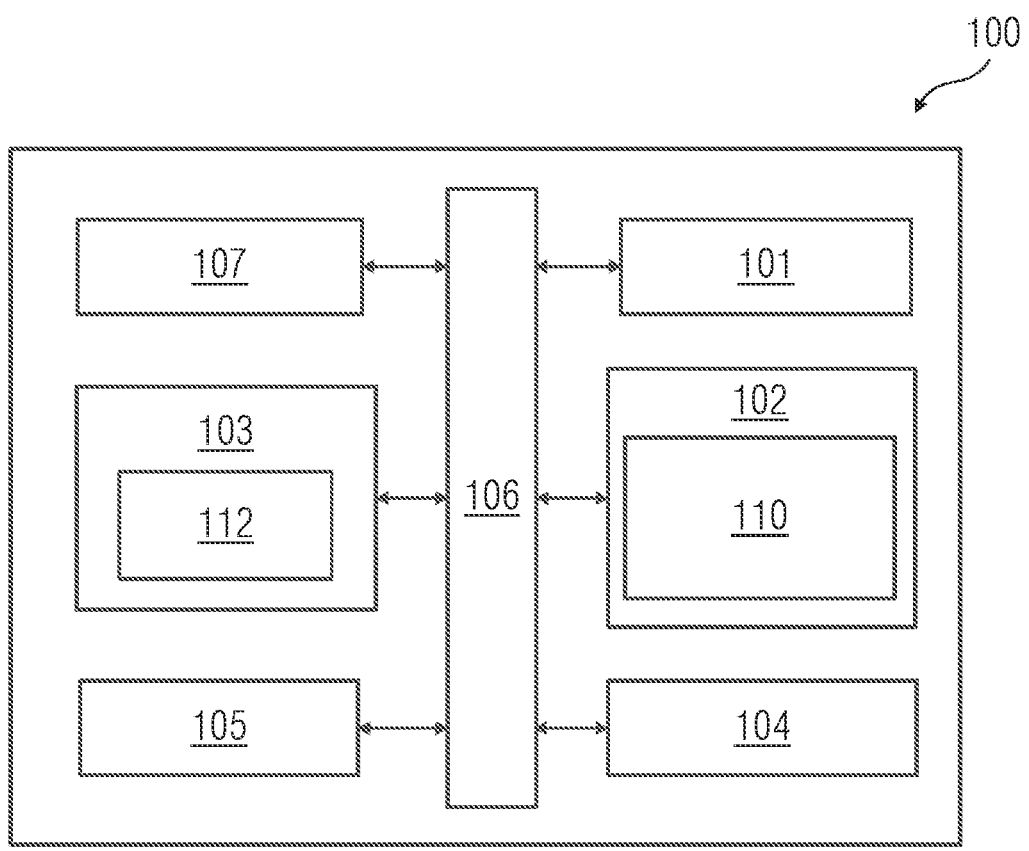
FIG. 1 illustrates a block diagram of a device in which an embodiment for determining a presence of tumor in a patient may be implemented.

Hereinafter, embodiments for carrying out the present invention are described in detail. The various embodiments are described with reference to the drawings, where like reference numerals are used to refer to like elements throughout. In the following description, for purpose of explanation, numerous specific details are set forth in order to provide a thorough understanding of one or more embodiments. It may be evident that such embodiments may be practiced without these specific details.

Features, advantages, or alternative embodiments herein may be assigned to the other objects and vice versa. In other words, the providing systems may be improved with features described in the context of the methods. In this case, the functional features of the method are embodied by objective units of the providing system.

Further, in the following, the present embodiments are described with respect to methods and systems for determining a presence of a tumor in a patient as well as with respect to methods and systems for training a machine learning model for determining a presence of a tumor in a patient. Features, advantages, or alternative embodiments herein may be assigned to the other objects and vice versa. In other words, methods and systems for training the machine learning model for determining a presence of a tumor in a patient may be improved with features described in context of the methods and systems for determining a presence of a tumor in a patient, and vice versa. For example, the trained machine learning model of the methods and systems for determining a presence of a tumor in a patient may be adapted by the methods and systems for training the machine learning model for determining a presence of a tumor in a patient. Further, the input data may include advantageous features and embodiments of the training input data, and vice versa. Further, the output data may include advantageous features and embodiments of the output training data, and vice versa.

FIG. 1 is a block diagram of a device 100 in which an embodiment may be implemented, for example, as a device 100 for determining a presence of a tumor in a patient, configured to perform the processes as described therein. In FIG. 1, the device 100 includes a processing unit 101 (e.g., a processor), a memory 102, a storage unit 103, an input unit 104, a bus 106, an output unit 105, and a network interface 107.

The processing unit 101, as used herein, may be any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 101 may also include embedded controllers, such as generic or programmable logic devices or arrays, application specific integrated circuits, single-chip computers, and the like.

The memory 102 may be volatile memory and non-volatile memory. The memory 102 may be coupled for communication with the processing unit 101. The processing unit 101 may execute instructions and/or code stored in the memory 102. A variety of computer-readable storage media may be stored in and accessed from the memory 102. The memory 102 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 102 includes a tumor determination module 110 stored in the form of machine-readable instructions on any of the above-mentioned storage media and may be in communication to and executed by the processor 101. When executed by the processor 101, the tumor determination module 110 causes the processor 101 to process a medical image to determine a presence of a tumor in a patient. Method acts executed by the processor 101 to achieve the abovementioned functionality are elaborated upon in detail in FIGS. 2, 3, 4, 5, and 6.

The storage unit 103 may be a non-transitory storage medium that stores a medical database 112. The medical database 112 is a repository of medical images and tumor data related to one or more patients that is maintained by a healthcare service provider. The input unit 104 may include one or more input devices such as a keypad, a touch-sensitive display, a camera (e.g., a camera receiving gesture-based inputs), etc. capable of receiving input signal such as a medical image. The bus 106 acts as interconnect between the processor 101, the memory 102, the storage unit 103, the input unit 104, the output unit 105, and the network interface 107.

Those of ordinary skilled in the art will appreciate that the hardware depicted in FIG. 1 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter may also be used in addition to or in place of the hardware depicted. The depicted example is provided for the purpose of explanation only and is not meant to imply architectural limitations with respect to the present disclosure.

A device 100 in accordance with an embodiment includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through a pointing device. The position of the cursor may be changed, and/or an event such as clicking a mouse button may be generated to actuate a desired response.

One of various commercial operating systems, such as a version of Microsoft Windows™, a product of Microsoft Corporation located in Redmond, Washington may be employed if suitably modified. The operating system is modified or created in accordance with the present disclosure as described.

Disclosed embodiments provide systems and methods for processing medical images. For example, the systems and methods may enable determination of a presence of a tumor in a patient.

Figure 2:
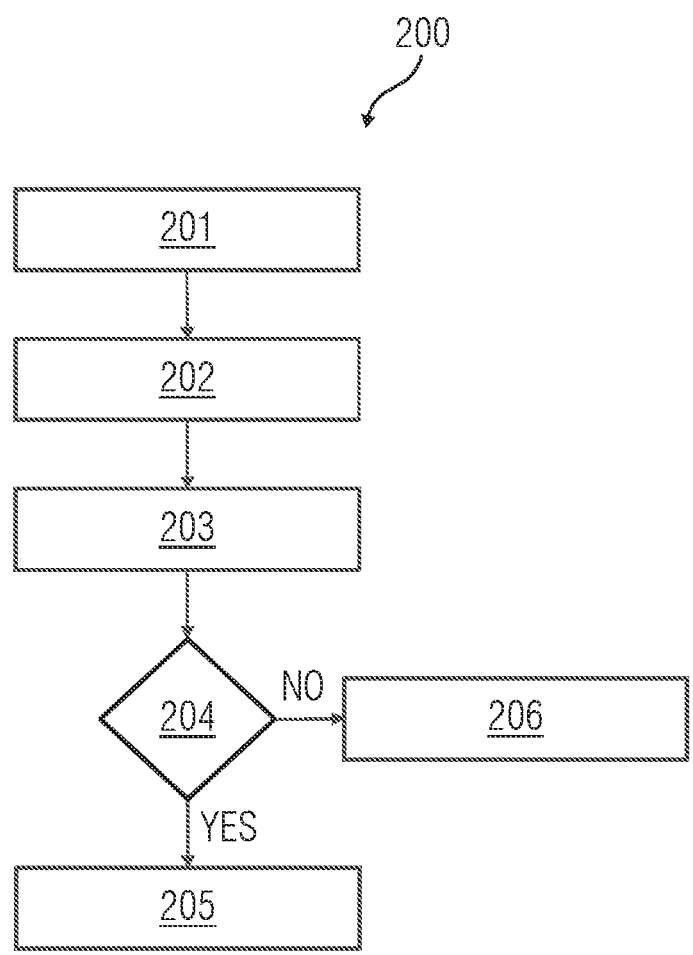
FIG. 2 illustrates a flowchart of a method of determining presence of a tumor in a patient, according to an embodiment.

FIG. 2 illustrates a flowchart of a method 200 of determining a presence of a tumor in a patient, according to an embodiment. At act 201, a medical image associated with the patient is received from a medical imaging device. The medical image is a computed tomography angiography image. In an alternate embodiment, the medical image may be obtained from any imaging modality that may image vasculature associated with the patient. The medical image depicts a region of interest associated with the patient. The region of interest may be a part of a body of the patient that may be suspected to have the tumor. The region of interest depicts, for example, an organ associated with the patient and associated vasculature. The method 200 further includes an act 202 where one or more blood vessels associated with the region of interest is identified. In an embodiment, the blood vessels may be identified using image segmentation techniques such as a region growing algorithm. The region growing algorithm identifies an object to be segmented based on a pixel information present in the medical image. In an alternate embodiment, the topology of the blood vessels may be preserved using topology preserving thinning algorithm. The algorithm enables emphasizing the topology of the blood vessels (e.g., length, direction, and width of the blood vessels).

At act 203, a set of characteristics associated with the blood vessels is determined. In an embodiment, the set of characteristics associated with the blood vessels include diameter associated with the blood vessels, branching of the blood vessels, and/or tortuosity of the blood vessels. The set of characteristics is determined using a trained machine learning model. The model is a classification and regression tree (CART) model. The model classifies the medical image as normal or suspected to include tumor with feeder vessels, based on the set of characteristics associated with the blood vessels. At act 204, it is determined if the blood vessels are feeder vessels associated with the tumor, based on the set of characteristics associated with the blood vessels. The CART model includes a root node, a plurality of child nodes, a plurality of branches, and leaf nodes, based on which a final decision is made by the model. The root node splits into child nodes. The leaf nodes include the output variable(s) based on which the model performs the prediction of presence of feeder vessels in the medical image. The model uses a metric named Gini index to create decision points for classification tasks performed by the model. Therefore, during a classification task, a weighted sum of Gini index associated with the child nodes is computed. This is performed for all child node splits, and the split with the lowest Gini index is chosen as the best split. The Gini index is computed using the below expression:

$$\text{Gini} = 1 - \sum_{i=1}^{n}(Pi)^2$$

where 'i' is the number of classes in the tree and 'Pi' is the probability of each class.

Further, at act 205, a tumor region is detected in the region of interest based on the feeder vessels associated with the tumor. This may be performed if the blood vessels are identified as feeder vessels. However, if the model determines no presence of feeder vessels at act 204, the medical image is determined to include no tumor/feeder vessels at act 206. The method acts associated with detecting the tumor region in the medical image is described in further detail in FIG. 5.

FIG. 3 illustrates a flowchart of a method 300 of determining if the blood vessels are feeder vessels associated with the tumor, according to an embodiment. At act 301, a diameter associated with the blood vessel is determined. Variations in diameter of blood vessels are recognized as indicators of an abnormal vasculature. The diameter of the blood vessel is calculated using Euclidian distance between points A and B on the blood vessel. The below expression is used to calculate the Euclidian distance:

$$\text{Diameter} = \sqrt{|X_A - X_B|^2 + |Y_A - Y_B|^2}$$

$X_A$ and $Y_A$ are cartesian coordinates of point A, and $X_B$ and $Y_B$ are cartesian coordinates of point B in Euclidean plane.

In a vasculature associated with a normal tissue, a diameter of the parent blood vessel is greater than a diameter of the branching blood vessels. Therefore, the diameter of the blood vessel decreases along the length of the blood vessel. At act, 302, it is determined if the diameter of the blood vessel decreases as the blood vessels branch into branching vessels, using the CART model. If the diameter of the blood vessel does not decrease, the blood vessel is classified as a feeder vessel by the CART model. However, if the diameter of the blood vessel decreases along the length of the blood vessel, the blood vessel is classified as normal (e.g., non-tumor vasculature) at act 304.

In an alternate embodiment, at act 304, radii associated with the blood vessel and the branching vessels associated with the blood vessel are determined. At act 305, a cube of the radius associated with the blood vessels and a respective cube of the radius associated with each of the branching vessels is computed. At act 306, it is determined if a sum of cubes of the radii associated with the branching vessels equals a sum of cubes of the radii associated with the blood vessels. Generally, branching vasculature of a circulatory system obeys Murray's law (e.g., the cube of the radius of the parent blood vessel equals the sum of cubes of the radii of the branching vessels).

$$r^3 = r_1^3 + r_2^3 + r_3^3 + \ldots + r_n^3$$

'r' is the radius of the blood vessel, and $r_1$ to $r_n$ are radii of the branching vessels.

Therefore, if Murray's law is obeyed by the vasculature, the blood flow in the vasculature is laminar. However, if Murray's law is not obeyed, the blood flow in the vasculature is turbulent and may be an indication of presence of feeder vessels in the region of interest. Therefore, if the sum of cubes of the radii associated with the branching vessels does not equal the cube of the radius associated with the blood vessel(s), the blood vessel is classified as the feeder vessel associated with the tumor at act 304. However, if the sum of the cubes of the radii associated with the branching vessels equals the cube of the radius associated with the blood vessel(s), the blood vessel is classified as normal (e.g., non-tumor vasculature) at act 307.

FIG. 4 illustrates a flowchart of yet another method 400 of determining if the blood vessels are feeder vessels associated with the tumor, according to an embodiment. At act 401, a length associated with the blood vessels is determined. The length of the blood vessel may be a path length associated with the blood vessels. At act 402, an angular value at each point of angulation of the blood vessel is determined. The points of angulation may be each deviation of the blood vessel from a straight path to be followed by the blood vessel. This is defined as the tortuosity of the blood vessel. In an embodiment, the tortuosity of the blood vessels is computed using Distance Metric method or Sum of Angles Metric (SOAM) method at act 403. According to the Sum of Angles Metric method, the below expression may be used for calculation of tortuosity:

$$SOAM = \frac{\Sigma_{k=0}^{n}(180 - \alpha)}{L1}$$

$\alpha$ is the angular deviation associated with the blood vessel in degrees, and L1 is the path length associated with the blood vessel.

At act 404, the measured tortuosity of the blood vessel is compared with a pre-determined standard associated with the blood vessels. For example, if there are more than two consecutive curvatures of angles greater than or equal to 180°, the blood vessel is classified as tortuous at act 405. However, if the tortuosity of the blood vessel is equal to or below the pre-determined standard, the blood vessel is classified as normal (e.g., non-tumor vasculature) at act 406. In an embodiment, tortuosity of the blood vessel may not be the only characteristic based on which the blood vessel is classified as feeder vessel. Tortuosity of the blood vessel may be considered along with other characteristics associated with the blood vessel such as diameter and branching of the blood vessels. This avoids false positive results.

FIG. 5 illustrates a flowchart of a method 500 of detecting the tumor region in the region of interest based on the feeder vessels, according to an embodiment. At act 501, a region in the medical image is identified based on the classified feeder vessels. For example, the region in the region of interest is identified based on where the feeder vessels drain. The area in the medical image where the feeder vessels taper off may be identified as the region where the feeder vessels drain. Additionally, at act 502, a pixel intensity associated with the region of interest is identified. The pixel intensity is the pixel values associated with the pixels of the medical image. At act 503, the tumor region is identified based on the pixel intensity and the region surrounding the feeder vessels. The region surrounding the feeder vessels is taken as an input to determine the tumor region. The pixel intensity associated with the region surrounding the feeder vessels is unique and different over the rest of the region of interest. Therefore, connected component labelling mechanism is used to accurately determine the tumor region.

FIG. 6 illustrates a flowchart of a method 600 of training a machine learning model to determine a presence of tumor in a patient, according to an embodiment. At act 601, a medical image associated with a patient is received. The medical image includes a region of interest that may be suspected to include a tumor. At act 602, one or more blood vessels associated with the region of interest is identified. At act 603, the machine learning model is received by the processing unit 101. At act 604, a set of characteristics associated with the blood vessels is determined by the machine learning model. Further, the machine learning model determines if the blood vessels are feeder vessels associated with the tumor based on the set of characteristics associated with the blood vessels at act 605.

At act 606, a tumor data related to the medical image is received, where the tumor data indicates if the blood vessels are feeder vessels associated with the tumor. In an embodiment, the tumor data includes medical image associated with the patient that has been pre-labelled to indicate presence or absence of feeder vessels. Alternatively, the tumor data may also include medical images from a plurality of patients historically examined for presence of feeder vessels/tumor. In a further embodiment, the tumor data may include medical images associated with a plurality of body parts associated with the patients.

At act 607, a comparison is made to determine if the output of the machine learning model matches the tumor data. A need to adjust the machine learning model is determined if the output of the model does not match the tumor data. Therefore, if the need to adjust the model is determined, the model is adjusted at act 608. The machine learning model is adjusted such that the accuracy with which the model predicts the presence of feeder vessels in the medical image is improved. In an alternative embodiment, if the output of the model does not match the tumor data, a notification may be generated for a user of the method to determine if the model is to be adjusted as per the tumor data. The model may be then adjusted based on the input of the user.

The advantage of the present embodiments is the method and device enable effective detection of tumor region in the medical image. Further, the present embodiments enable identification of right feeder vessels for embolization. Therefore, healthy tissues associated with the patient are not damaged due to cancer therapy. Additionally, the present embodiments reduce the need for manual identification of tumor region in the medical images. The present embodiments further enable targeted cancer therapy based on which the tumor blood vessel network may be embolized accurately. Further, the present embodiments enable multiple tumors to be embolized in one medical procedure.

The foregoing examples have been provided merely for the purpose of explanation and are in no way to be construed as limiting of the present e disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods, and uses, such as are within the scope of the appended claims. Those skilled in the art, having the benefit of the teachings of this specification, may effect numerous modifications thereto, and changes may be made without departing from the scope and spirit of the invention in its aspects.

What is claimed is:

1. A method of determining a presence of a tumor in a patient, the method comprising:
    receiving, by a processing unit, a medical image associated with the patient, wherein the medical image comprises a region of interest associated with the patient;
    identifying, by the processing unit, one or more blood vessels associated with the region of interest in the medical image;
    determining, by the processing unit, a set of characteristics associated with the one or more blood vessels using a trained machine learning model;
    determining, by the trained machine learning model, whether the one or more blood vessels are feeder vessels associated with the tumor based on the set of characteristics associated with the one or more blood vessels; and
    detecting, by the processing unit, a tumor region in the region of interest based on the feeder vessels when the one or more blood vessels are the feeder vessels associated with the tumor,
    wherein determining whether the one or more blood vessels are the feeder vessels associated with the tumor comprises:
        determining one or more radii associated with the one or more blood vessels, respectively, using a trained machine learning model;
        determining radii associated with branching vessels originating from the one or more blood vessels, respectively, using the trained machine learning model;
        computing one or more cubes of the one or more radii associated with the one or more blood vessels, respectively, and cubes of the radii associated with the branching vessels, respectively, using the trained machine learning model;
        determining when a sum of the cubes of the radii associated with the branching vessels equals a sum of the one or more cubes of the one or more radii associated with the one or more blood vessels using the trained machine learning model; and
        classifying the one or more blood vessels as the feeder vessels when the sum of the cubes of the radii associated with the branching vessels does not equal the sum of the one or more cubes of the one or more radii associated with the one or more blood vessels using the trained machine learning model.

2. The method of claim 1, wherein the set of characteristics associated with the one or more blood vessels comprises a diameter associated with the one or more blood vessels, branching of the one or more blood vessels, tortuosity of the one or more blood vessels, or any combination thereof.

3. The method of claim 1, wherein determining whether the one or more blood vessels are the feeder vessels associated with the tumor comprises:
    measuring a diameter associated with the one or more blood vessels using the trained machine learning model;
    determining whether the diameter associated with the one or more blood vessels decreases as the one or more blood vessels branch into branching vessels using the trained machine learning model; and
    classifying the one or more blood vessels to be the feeder vessels associated with the tumor when the diameter associated with the one or more blood vessels does not decrease as the one or more blood vessels branch into the branching vessels using the trained machine learning model.

4. The method of claim 1, wherein determining whether the one or more blood vessels are the feeder vessels associated with the tumor comprises:
    determining a tortuosity of the one or more blood vessels using the trained machine learning model, wherein the tortuosity of the one or more blood vessels is determined based on angular deviation of the one or more blood vessels from a straight path associated with the one or more blood vessels;
    comparing, using the trained machine learning model, the tortuosity of the one or more blood vessels with a pre-determined standard associated with the one or more blood vessels; and
    classifying, using the trained machine learning model, the one or more blood vessels as the feeder vessels when the tortuosity of the one or more blood vessels does not match the pre-determined standard.

5. The method of claim 1, wherein detecting the tumor region in the region of interest based on the feeder vessels comprises:
    identifying a region in the medical image based on the feeder vessels, wherein the identified region in the medical image is an area surrounding the feeder vessels;
    determining a pixel intensity associated with the region of interest in the medical image; and
    determining the tumor region based on the pixel intensity and the region surrounding the feeder vessels, wherein the tumor region has a pixel intensity greater than a pixel intensity of other regions in the medical image.

6. The method of claim 1, wherein identifying the one or more blood vessels associated with the region of interest in the medical image comprises segmenting the one or more blood vessels using a segmentation algorithm.

7. The method of claim 6, further comprising preserving a topology of the one or more blood vessels using a topology preserving thinning algorithm.

8. The method of claim 1 wherein the trained machine learning model is a classification and regression tree (CART) model.

9. A method of training a machine learning model for determining a presence of a tumor in a patient, the method comprising:
receiving, by a processing unit, a medical image associated with a patient, wherein the medical image comprises a region of interest associated with the patient;
identifying, by the processing unit, one or more blood vessels associated with the region of interest;
receiving, by the processing unit, the machine learning model;
determining, by the machine learning model, a set of characteristics associated with the one or more blood vessels;
determining, by the machine learning model, whether the blood vessels are feeder vessels associated with the tumor based on the set of characteristics associated with the one or more blood vessels;
receiving, by the processing unit, tumor data related to the medical image, wherein the tumor data indicates whether the one or more blood vessels are the feeder vessels associated with the tumor; and
adjusting the machine learning model based on an outcome of a comparison between the feeder vessels determined by the machine learning model and the tumor data,
wherein determining whether the blood vessels are the feeder vessels associated with the tumor comprises:
determining radii associated with the blood vessels, respectively, using the machine learning model;
determining radii associated with branching vessels originating from the blood vessels, respectively, using the machine learning model;
computing cubes of the radii associated with the blood vessels, respectively, and cubes of the radii associated with the branching vessels, respectively, using the machine learning model;
determining when a sum of the cubes of the radii associated with the branching vessels equals a sum of the cubes of the radii associated with the blood vessels using the machine learning model; and
classifying the blood vessels as the feeder vessels when the sum of the cubes of the radii associated with the branching vessels does not equal the sum of the cubes of the radii associated with the blood vessels using the machine learning model.

10. The method of claim 9, wherein the tumor data comprises the medical image labelled to indicate presence or absence of the feeder vessels associated with the tumor in the patient.

11. A device for determining a presence of a tumor in a patient, the device comprising:
one or more processing units;
a medical database coupled to the one or more processing units, the medical database comprising a plurality of medical images associated with the patient and tumor data; and
a memory coupled to the one or more processing units, the memory comprising a tumor determination module configured to:
receive a medical image associated with the patient, wherein the medical image comprises a region of interest associated with the patient;
identify one or more blood vessels associated with the region of interest in the medical image;
determine a set of characteristics associated with the one or more blood vessels using a trained machine learning model;
determine, using the trained machine learning model, whether the blood vessels are feeder vessels associated with the tumor based on the set of characteristics associated with the one or more blood vessels; and
detect a tumor region in the region of interest based on the feeder vessels when the blood vessels are the feeder vessels associated with the tumor,
wherein the determination of whether the one or more blood vessels are the feeder vessels associated with the tumor comprises:
determination of one or more radii associated with the one or more blood vessels, respectively, using a trained machine learning model;
determination of radii associated with branching vessels originating from the one or more blood vessels, respectively, using the trained machine learning model;
computation of one or more cubes of the one or more radii associated with the one or more blood vessels, respectively, and cubes of the radii associated with the branching vessels, respectively, using the trained machine learning model;
determination of whether a sum of the cubes of the radii associated with the branching vessels equals a sum of the one or more cubes of the one or more radii associated with the one or more blood vessels using the trained machine learning model; and
classification of the one or more blood vessel as the feeder vessels when the sum of cubes of the radii associated with the branching vessels does not equal the sum of the one or more cubes of the one or more radii associated with the one or more blood vessels using the trained machine learning model.

12. The device of claim 11, wherein the determination of whether the one or more blood vessels are the feeder vessels associated with the tumor comprises:
measurement of a diameter associated with the one or more blood vessels using the trained machine learning model;
determination of whether the diameter associated with the one or more blood vessels decreases as the one or more blood vessels branch into branching vessels using the trained machine learning model; and
classification of the one or more blood vessels to be the feeder vessels associated with the tumor when the diameter associated with the one or more blood vessels does not decrease as the one or more blood vessels branch into the branching vessels, using the trained machine learning model.

13. The device of claim 11, wherein the determination of whether the blood vessels are the feeder vessels associated with the tumor comprises:
determination, using the trained machine learning model, of a tortuosity of the one or more blood vessels, wherein the tortuosity of the one or more blood vessels is determined based on angular deviation of the one or more blood vessels from a straight path associated with the one or more blood vessels;
comparison, using the trained machine learning model, of the tortuosity of the one or more blood vessels with a pre-determined standard associated with the one or more blood vessels; and
classification, using the trained machine learning model, of the one or more blood vessels as the feeder vessels when the tortuosity of the one or more blood vessels does not match the pre-determined standard.

14. The device of claim 11, wherein the detection of the tumor region in the region of interest based on the feeder vessels comprises:
- identification of a region in the medical image based on the feeder vessels, wherein the identified region in the medical image is an area surrounding the feeder vessels;
- determination of a pixel intensity associated with the region of interest in the medical image; and
- determination of the tumor region based on the pixel intensity and the region surrounding the feeder vessels, wherein the tumor region has a pixel intensity greater than a pixel intensity of other regions in the medical image.

15. The device of claim 11, wherein the identification of the one or more blood vessels associated with the region of interest in the medical image comprises segmentation of the one or more blood vessels using a segmentation algorithm.

16. The device of claim 15, wherein the tumor determination module is further configured to preserve a topology of the one or more blood vessels using a topology preserving thinning algorithm.

17. A non-transitory computer readable storage medium that stores machine-readable instructions executable by a processor to determine a presence of a tumor in a patient, the machine-readable instructions comprising:
- receiving a medical image associated with the patient, wherein the medical image comprises a region of interest associated with the patient;
- identifying one or more blood vessels associated with the region of interest in the medical image;
- determining a set of characteristics associated with the one or more blood vessels using a trained machine learning model;
- determining, using the trained machine learning model, whether the one or more blood vessels are feeder vessels associated with the tumor based on the set of characteristics associated with the one or more blood vessels; and
- detecting a tumor region in the region of interest based on the feeder vessels when the one or more blood vessels are the feeder vessels associated with the tumor, wherein determining whether the one or more blood vessels are the feeder vessels associated with the tumor comprises:
- determining one or more radii associated with the one or more blood vessels, respectively, using a trained machine learning model;
- determining radii associated with branching vessels originating from the one or more blood vessels, respectively, using the trained machine learning model;
- computing one or more cubes of the one or more radii associated with the one or more blood vessels, respectively, and cubes of the radii associated with the branching vessels, respectively, using the trained machine learning model;
- determining when a sum of the cubes of the radii associated with the branching vessels equals a sum of the one or more cubes of the one or more radii associated with the one or more blood vessels using the trained machine learning model; and
- classifying the one or more blood vessels as the feeder vessels when the sum of the cubes of the radii associated with the branching vessels does not equal the sum of the one or more cubes of the one or more radii associated with the one or more blood vessels using the trained machine learning model.

* * * * *